United States Patent
Shibata (10) Patent No.: US 11,055,877 B2
(45) Date of Patent: Jul. 6, 2021

(54) IMAGE PROCESSING DEVICE, IMAGE PROCESSING METHOD, AND PROGRAM STORAGE MEDIUM

(71) Applicant: NEC Corporation, Tokyo (JP)

(72) Inventor: Takashi Shibata, Tokyo (JP)

(73) Assignee: NEC CORPORATION, Tokyo (JP)

( * ) Notice: Subject to any disclaimer, the term of this patent is extended or adjusted under 35 U.S.C. 154(b) by 8 days.

(21) Appl. No.: 16/629,095

(22) PCT Filed: Jul. 13, 2017

(86) PCT No.: PCT/JP2017/025542
§ 371 (c)(1),
(2) Date: Jan. 7, 2020

(87) PCT Pub. No.: WO2019/012647
PCT Pub. Date: Jan. 17, 2019

(65) Prior Publication Data
US 2020/0193644 A1    Jun. 18, 2020

(51) Int. Cl.
*G06T 7/90* (2017.01)
*G06T 5/50* (2006.01)

(52) U.S. Cl.
CPC .................. *G06T 7/90* (2017.01); *G06T 5/50* (2013.01); *G06T 2207/10024* (2013.01); *G06T 2207/20221* (2013.01)

(58) Field of Classification Search
CPC combination set(s) only.
See application file for complete search history.

(56) References Cited

U.S. PATENT DOCUMENTS

| 2003/0228064 A1* | 12/2003 | Gindele | G06T 5/50 |
| | | | 382/260 |
| 2005/0276504 A1* | 12/2005 | Chui | G06T 5/20 |
| | | | 382/264 |

(Continued)

FOREIGN PATENT DOCUMENTS

| JP | 2010-166363 A | 7/2010 |
| JP | 2012-027773 A | 2/2012 |

(Continued)

OTHER PUBLICATIONS

Zhiqiang Zhou, "Multi-scale weighted gradient-based fusion for multi-focus images," ScienceDirect,Information Fusion 20 (2014) 60-72,Jan. 7, 2014, pp. 61-70.*

(Continued)

*Primary Examiner* — Omar S Ismail (57) ABSTRACT

A gradient calculation unit calculates an image gradient on a pixel-by-pixel basis in each of a plurality of images. A scale search unit calculates a scale score based on degree of spatial frequency components for each pixel in each of the images. A gradient score calculation unit calculates, for each pixel, a gradient score on the basis of the image gradient and the scale score. A gradient finalization unit calculates, using the gradient score and, as a target gradient, an image gradient of each pixel in a combined image. On the basis of the target gradient, a coefficient calculation unit calculates, for each pixel of the combined image, a coefficient of base vectors constituting a preset base vector group in the combined image. A combining unit generates the combined image through linear combination of the base vectors based on the calculated coefficients.

7 Claims, 4 Drawing Sheets

(56) References Cited

U.S. PATENT DOCUMENTS

| | | | |
|---|---|---|---|
| 2006/0110072 A1* | 5/2006 | Domera-Venkata | G06T 5/50 382/299 |
| 2010/0183225 A1* | 7/2010 | Vantaram | G06T 7/155 382/173 |
| 2012/0127297 A1* | 5/2012 | Baxi | G06K 9/036 348/79 |
| 2013/0071028 A1* | 3/2013 | Schiller | G06T 7/11 382/180 |
| 2013/0250123 A1 | 9/2013 | Zhang et al. | |
| 2018/0130188 A1* | 5/2018 | Farrell | G06T 7/90 |

FOREIGN PATENT DOCUMENTS

| | | |
|---|---|---|
| JP | 2015-502058 A | 1/2015 |
| JP | 2016-032289 A | 3/2016 |
| JP | 2017-011633 A | 1/2017 |

OTHER PUBLICATIONS

Huiguang Yang,"Automaticsegmentationofgranularobjectsinimages:Combining local densityclusteringandgradient-barrierwatershed," ScienceDirect,Pattern Recognition 47(2014)2266-2279, Nov. 20, 2013, pp. 2266-2271.*

Weiwei Sun,"Fully Convolutional Networks for Semantic Segmentation of Very High Resolution Remotely Sensed Images Combined With DSM," IEEE Geoscience and Remote Sensing Letters, vol. 15, No. 3, Mar. 2018, pp. 474-478.*

Dong-O Kim,"Gradient Information-Based Image Quality Metric," IEEE Transactions on Consumer Electronics, vol. 56, No. 2, May 2010,pp. 930-932.*

Wei Zhang,"Gradient-directed Composition of Multi-exposure Images," 2010 IEEE Computer Society Conference on Computer Vision and Pattern Recognition,Jun. 13-18, 2010,pp. 530-535.*

John J. Lewis,"Pixel-and region-based image fusion with complex wavelets," cienceDirect,Information Fusion 8 (2007) 60-72,Nov. 23, 2005, pp. 120-127.*

International Search Report for PCT Application No. PCT/JP2017/025542, dated Oct. 3, 2017.

English translation of Written opinion for PCT Application No. PCT/JP2017/025542.

Graham D. Finlayson, David Connah and Mark S. Drew, "Lookup-Table-Based Gradient Field Reconstruction", IEEE Transactions on Image Processing, vol. 20, Issue 10, Oct. 2011, p. 2827-2836, USA.

* cited by examiner

IMAGE PROCESSING DEVICE, IMAGE PROCESSING METHOD, AND PROGRAM STORAGE MEDIUM

This application is a National Stage Entry of PCT/JP2017/025542 filed on Jul. 13, 2017, the contents of all of which are incorporated herein by reference, in their entirety.

TECHNICAL FIELD

The present invention relates to a technique for combining a plurality of images.

BACKGROUND ART

In recent years, various image combining methods have been proposed. Further, a camera capable of changing settings (exposure amount and exposure time) related to capturing enables to acquire various images having different sensitivity characteristics with respect to a wavelength band of light. In addition, even when the setting such as the exposure time is the same, a substantially different image is acquired by a camera depending on whether a flash is used during capturing. Furthermore, in order to capture various target objects, a camera using a sensor according to an object is widely used. For example, a surveillance camera using a visible light sensor is widely used in order to monitor a person and the like. A camera equipped with a sensor using invisible light such as a near infrared ray and a far infrared ray is also widely used for nighttime surveillance. In addition, a near ultraviolet ray camera is also commercially available. An apparatus that captures a wavelength longer than the visible light wavelength band such as terahertz wave or radio wave is also commercially available.

Such various image devices spread widely in this manner, and thus an image processing technique has been developed for applying a plurality of captured images having different wavelength bands to many fields such as medical care and security. PTL 1 discloses a technique of combining a visible light image and a near-infrared image with a same capturing area and capturing timing. In the technique disclosed in PTL 1, when a visible light image and a near-infrared image are combined, luminance information of the visible light image and luminance information of the near-infrared image are compared in each pixel, and the higher luminance information is selected as the luminance information of the pixel in the combined image. Further, NPL 1 discloses a technique of, when a plurality of images are combined, generating a combined image by using an image gradient (information on a difference in pixel value between adjacent pixels) of each pixel in the image.

CITATION LIST

Patent Literature

[PTL 1] Japanese Unexamined Patent Application Publication No. 2010-166363

Non Patent Literature

[NPL1] Graham D. Finlayson, David Connah and Mark S. Drew, "Lookup-table-based Gradient Field Reconstruction", IEEE Transactions on Image Processing, Volume 20, Issue 10, October 2011, pages 2827 to 2836

SUMMARY OF INVENTION

Technical Problem

Incidentally, performing image processing by using image gradient information enables to acquire easily image quality suitable for a purpose of an image after the image processing, and the image quality of the image can be improved according to the purpose. NPL 1 discloses a technique of combining images by using image gradient information. However, in NPL 1, the following problem may occur.

Specifically, in the technique disclosed in NPL 1, an image gradient is calculated for each pixel in each of a plurality of images to be combined. Then, by using a calculated value acquired by the sum of the image gradients of associated pixels in each image to be combined, an image gradient for each pixel in the combined image after combining a plurality of images to be combined is calculated. In this manner, the combined image is generated by using even information on the image gradients to be calculated.

In such a method, however, when the combined image is generated, the calculated value by the sum of the image gradients is used, and therefore information on locally large image gradients is easily reflected in the combined image. Meanwhile, information on small image gradients that changes globally such as gradation is difficult to be reflected in the combined image. For example, a far-infrared image has less texture and the image gradient is small as a whole. When an image with such a small image gradient as a far-infrared image and a visible light image with a larger image gradient than the image are combined by the method disclosed in NPL 1, a combined image in which information on the image with a small image gradient is hardly reflected is generated. For this reason, a problem occurs that, for example, it is difficult to analyze an event captured in a far-infrared image (in other words, an image by a far-infrared sensor) by using a combined image acquired by superposing the far-infrared image on a visible light image.

The present invention has been conceived in order to solve the above-described problem. Specifically, a main object of the present invention is to provide a technique capable of generating, when a plurality of images are combined by using information on an image gradient, a combined image in which information on an image with a small image gradient is also reflected, and improving image quality required for the combined image.

Solution to Problem

To achieve the main object of the present invention, an image processing device of the present invention, as an aspect, includes:

a gradient calculation unit that calculates an image gradient for each pixel in each of a plurality of images to be combined;

a scale search unit that calculates a scale score based on an inclusion degree of a spatial frequency component for the each pixel in the each of the plurality of images to be combined;

a gradient score calculation unit that calculates, for the each pixel, a gradient score depending on the calculated image gradient and the calculated scale score;

a gradient finalization unit that compares the gradient scores of associated pixels in the plurality of images to be combined, and calculates a target gradient for each pixel in a combined image after combining the plurality of images to be combined, the target gradient being the image gradient depending on the gradient score of the image having the larger gradient score than other images among the plurality of images to be combined;

a coefficient calculation unit that calculates, for the each pixel of the combined image, a coefficient of a base vector constituting a base vector group predetermined in the combined image based on the target gradient; and a combination unit that generates the combined image by linear combination of the base vector based on the calculated coefficient.

An image processing method of the present invention, as an aspect, includes:

calculating an image gradient for each pixel in each of a plurality of images to be combined;

calculating a scale score based on an inclusion degree of a spatial frequency component for the each pixel in the each of the images to be combined;

calculating, for the each pixel, a gradient score depending on the calculated image gradient and the calculated scale score;

comparing the gradient scores of associated pixels in the plurality of images to be combined, and calculating a target gradient for each pixel in a combined image after combining the plurality of images to be combined, the target gradient being the image gradient depending on the gradient score of the image having the larger gradient score than other images among the plurality of images to be combined;

calculating, for the each pixel of the combined image, a coefficient of a base vector constituting a base vector group predetermined in the combined image based on the target gradient; and generating the combined image by linear combination of the base vector based on the calculated coefficient.

A program storage medium of the present invention stores a computer program that, as an aspect, causes a computer to execute:

calculating an image gradient for each pixel in each of a plurality of images to be combined;

calculating a scale score based on an inclusion degree of a spatial frequency component for the each pixel in the each of the images to be combined;

calculating, for the each pixel, a gradient score depending on the calculated image gradient and the calculated scale score;

comparing the gradient scores of associated pixels in the plurality of images to be combined, and calculating a target gradient for each pixel in a combined image after combining the plurality of images to be combined, the target gradient being the image gradient depending on the gradient score of the image having the larger gradient score than other images among the plurality of images to be combined;

calculating, for the each pixel of the combined image, a coefficient of a base vector constituting a base vector group predetermined in the combined image based on the target gradient; and generating the combined image by linear combination of the base vector based on the calculated coefficient.

Advantageous Effects of Invention

The present invention is able to generate, when a plurality of images are combined by using information on an image gradient, a combined image in which information on an image with a small image gradient is also reflected, and improve image quality required for the combined image.

EXAMPLE EMBODIMENT

Example embodiments according to the present invention are described below, based on the drawings.

First Example Embodiment

Figure 1:
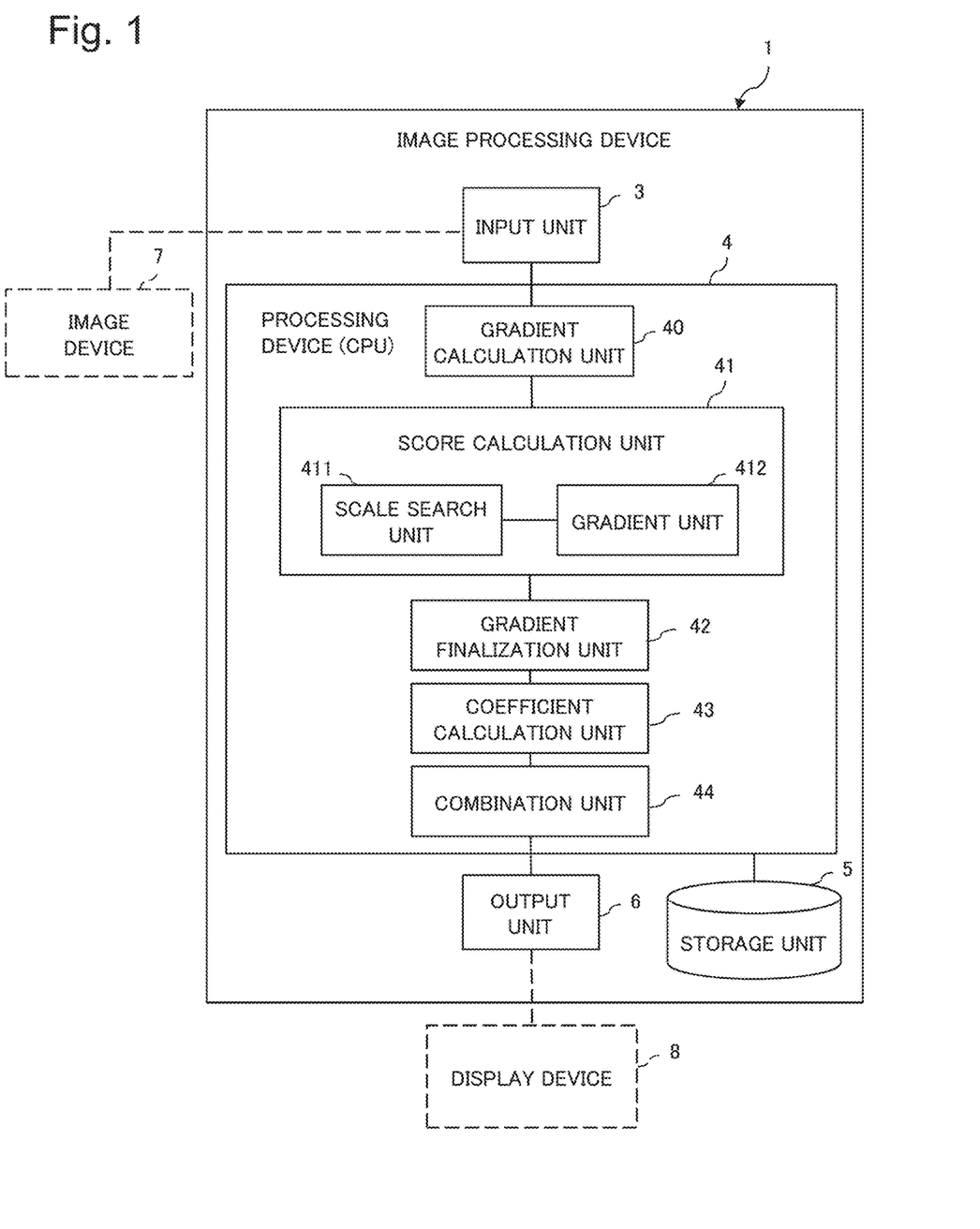
FIG. 1 is a block diagram simplistically illustrating a configuration of an image processing device according to a first example embodiment of the present invention.

FIG. 1 is a block diagram illustrating a configuration of an image processing device according to a first example embodiment of the present invention. An image processing device 1 according to the first example embodiment includes an input unit 3, a processing device 4, a storage unit 5, and an output unit 6.

The input unit 3 is an interface device and, for example, is connected to an image device 7 and has an interface function of receiving an image output from the image device 7. According to the first example embodiment, the image device 7 being connected to the input unit 3 is a device (an image device with a near infrared sensor) capable of capturing visible light and near infrared, and has a function of outputting a visible light image (hereinafter, also referred to as a scalar image) and a near-infrared image. The scalar image and the near-infrared image output from the image device 7 have almost a same capturing range, and herein, it is assumed that the capturing ranges are considered to be coincident.

Note that, the image device being connected to the input unit 3 is not limited to the image device capable of capturing visible light and near infrared, and, for example, an image device that captures visible light and an image device (also referred to as a near-infrared sensor) that captures near infrared may be also connected to the input unit 3. Further, instead of an image device being connected, a storage may be connected to the input unit 3. In this case, for example, a scalar image and a near-infrared image captured by an image device are stored in the storage, and the input unit 3 may receive the scalar image and the near-infrared image read from the storage by, for example, a function of the processing device 4.

The storage unit 5 includes a storage medium and has a configuration capable of storing various data and computer programs (programs). There are various types of storages including a storage medium such as a hard disk device and a semiconductor memory, and herein, a plurality of types of storages mounted on the image processing device 1 are collectively represented as the storage unit 5.

According to the first example embodiment, the captured images (the scalar image and the near-infrared image) received by the input unit 3 are registered in the storage unit 5 by the processing device 4.

In addition, the storage unit 5 stores information on a predetermined base vector group Φ. Herein, the base vector group Φ is a group of a plurality of base vectors $\varphi_j$ ("j" is an integer greater than or equal to 1) set to a combined image, when combining the scalar image and the near-infrared image to be combined. Note that "j" of the base vector $\varphi_j$ is information for identifying the base vector, and herein, indicates an order of arrangement in a case where the base vector group Φ is represented in a predetermined order in such a way that a plurality of base vectors constituting the base vector group Φ are represented as Φ={φ1, φ2, φ3, . . . }.

For example, it is assumed that channels of the scalar image input to the input unit 3 are red (R), green (G), and blue (B), and the channel of the near-infrared image is near infrared (N). In this case, the base vector group $\Phi_i$ representing a pixel value of each pixel i in a combined image (hereinafter, also simply referred to as a combined image) of the scalar image and the near-infrared image is set by the following equation (1), for example.

$$\Phi_i = \{\varphi_{ji}\}$$
$$= \{R_i, G_i, B_i, N_i, R_i^2, G_i^2, B_i^2, N_i^2, R_i*B_i, R_i*G_i, G_i*B_i,$$
$$R_i*N_i, G_i*N_i, B_i*N_i\}$$

Equation (1)

Note that "i" in the equation (1) is an integer greater than or equal to 1 and represents information for identifying each pixel in the scalar image, the near-infrared image, or the combined image. Herein, "i" represents an order of the pixels in case of raster scanning the image. Further, "*" in the equation (1) is a multiplication symbol. Further, "j" in "$\varphi_{ji}$" is information for identifying a base vector, similarly to "j" described above. For example, when the base vector group $\Phi_i$ is represented as the equation (1), a base vector $\varphi_{3i}$ (j=3) in the pixel i, for example, is "$B_i$", and a base vector $\varphi_{9i}$ (j=9) is "$R_i*B_i$".

Note that the base vector group $\Phi_i$ represented in the equation (1) is one example and the base vector group $\Phi_i$ is not limited to the equation (1). For example, the base vector $\varphi_{ji}$ constituting the base vector group $\Phi_i$ may be smaller than the equation (1), or a base vector such as $R_i^3$, $G_i^3$, $B_i^3$, and $N_i^3$ may be further added to the equation (1). The base vector $\varphi_{ji}$ constituting the base vector group $\Phi_i$ is appropriately set in consideration of a resolution and the like required for a combined image. Further, in consideration of information on the pixel value and the like included in each image to be combined, a plurality of base vector groups Φ having different combinations of base vectors $\varphi_i$ may be set and stored in the storage unit 5. In this case, for example, the base vector group Φ used for processing may be alternatively selected according to the image quality or the like requested by a user of the device.

When generating a combined image, a coefficient of each base vector $\varphi_{ji}$ constituting the above-described base vector group $\Phi_i$ of each pixel in the combined image is determined based on the scalar image and the near-infrared image (input image), thereby determining the pixel value of each pixel in the combined image and thus the combined image can be generated. The first example embodiment is characterized by a method of calculating a coefficient of each base vector $\varphi_{ji}$ in the combined image and the image processing device (processing device 4) for processing thereof.

The processing device 4 is configured by, for example, one or more central processing units (CPUs). According to the first example embodiment, the processing device 4 can have the following functions by reading and executing a computer program stored in the storage unit 5. Specifically, the processing device 4 includes, as a function unit, a gradient calculation unit 40, a score calculation unit 41, a gradient finalization unit 42, a coefficient calculation unit 43, and a combination unit 44.

The gradient calculation unit 40 has a function of calculating an image gradient as information representing a feature of each pixel. The image gradient is information on a difference in pixel value between adjacent pixels. Various methods have been proposed for calculating the image gradient. Herein, an appropriate method is employed in consideration of matters such as image quality required for a combined image and the processing capability of the processing device 4. The gradient calculation unit 40 calculates the image gradient of each pixel in each of the scalar image and the near-infrared image received by the input unit 3, based on the employed gradient calculation method.

Note that, according to the first example embodiment, in each pixel i, the image gradient is calculated for each component (channel) of a pixel value in consideration of each base vector $\varphi_{ji}$ constituting the base vector group $\Phi_i$. For example, when the base vector group $\Phi_i$ is set as the equation (1) described above, the image gradient is calculated for each pixel with regard to a red (R) component, a green (G) component, a blue (B) component, and a near infrared (N) component. Herein, the image gradients with regard to the red (R) component, the green (G) component, the blue (B) component, and the near infrared (N) component calculated by the gradient calculation unit 40 are also represented as $\Delta R_i$, $\Delta G_i$, $\Delta B_i$ and $\Delta N_i$ for each pixel. Note that "i" represents information for identifying a pixel, similarly to "i" in the equation (1). Hereinafter, "i" in the description represents information for identifying a pixel similarly.

The score calculation unit 41 has a function of calculating a score that represents a feature of each pixel by a numerical value in the scalar image and the near-infrared image. In the image processing device 1, the score calculation unit 41 includes a scale search unit 411 and a gradient unit (a gradient score calculation unit) 412. The scale search unit 411 has a function of calculating a score (hereinafter, for convenience, also referred to as a scale score) based on a scale (hereinafter, also simply referred to as scale) related to an inclusion degree of a spatial frequency component in each pixel in the scalar image and the near-infrared image. For example, the scale search unit 411 calculates the scale score for each pixel by using a scale space method that decomposes an image into images for each spatial frequency, based on a pixel value. More specifically, the scale search unit 411 changes, for each pixel, a value of "σ" in the Laplacian of Gaussian (LoG) operator represented by the following equation (2) proposed by Lindeberg et al., and calculates the largest LoG value as the scale score in each pixel.

$$LoG = f(\sigma) = -\frac{x^2 + y^2 - 2\sigma^2}{2\pi\sigma^6} \times \exp\left(-\frac{x^2 + y^2}{2\sigma^2}\right)$$

Equation (2)

Note that "σ" in the equation (2) represents a scale. Further, "x" represents, when a position of each pixel in an image (input image) input to the input unit 3 is represented by using a two-dimensional orthogonal coordinate system with x and y, a distance in the x-axis direction from a reference pixel, and "y" represents a distance in the y-axis direction from the reference pixel.

In addition, according to the first example embodiment, the scale search unit 411 calculates the scale score for each component (channel) of the pixel value in consideration of each base vector $\varphi_{ji}$ constituting the predetermined base vector group $\Phi_i$. For example, when the base vector group $\Phi_i$ is set as the equation (1) described above, the scale search unit 411 calculates, for each pixel, the scale scores with regard to the red (R) component, the green (G) component, the blue (B) component, and the near infrared (N) component. Herein, the scale scores calculated by the scale search unit 411 are also represented as $s_{Ri}$, $s_{Gi}$, $s_{Bi}$, and $s_{Ni}$.

Note that the method of calculating the scale score by the scale search unit 411 is not limited to the method by using the LoG operator described above. For example, as a method of calculating the scale score, a method of which a value acquired by multiplying the maximum value of f (σ) represented in the equation (2) by the value of a monotonously increasing function or a monotonously decreasing function having σ (scale) as a variable is set as the scale score may be employed. Alternatively, as a method of calculating the scale score, a method of which the maximum value of f (σ) represented in an equation (3) is set as the scale score may be employed.

$$f(\sigma) = -\exp\left(-\frac{x^2 + y^2}{2\sigma^2}\right) \quad \text{Equation (3)}$$

The gradient unit 412 has a function of calculating a score (hereinafter, referred to as a gradient score), based on a gradient in each pixel, in consideration of the scale score calculated by the scale search unit 411 in the scalar image and the near-infrared image. For example, data of an equation that has the image gradient calculated by the gradient calculation unit 40 and the scale score calculated by the scale search unit 411 as variables and calculates a value depending on magnitude of the image gradient and the scale score are given in the storage unit 5 in advance. The gradient unit 412 calculates the gradient score for each component of the pixel value in consideration of the base vector $\varphi_{ji}$ constituting the base vector group $\Phi_i$ in each pixel by using the data in each of the scalar image and the near-infrared image. As a specific example, when the base vector group $\Phi_i$ is set as the equation (1) described above, the gradient scores are calculated, for each pixel i, with regard to the red (R) component, the green (G) component, the blue (B) component, and the near infrared (N) component. In other words, it is assumed that the image gradients $\Delta R_i$, $\Delta G_i$, $\Delta B_i$ and $\Delta N_i$ with regard to the red (R) component, the green (G) component, the blue (B) component, and the near infrared (N) component are calculated in each pixel i by the gradient calculation unit 40. In addition, it is assumed that the scale scores $s_{Ri}$, $s_{Gi}$, $s_{Bi}$, and $s_{Ni}$ with regard to the red (R) component, the green (G) component, the blue (B) component, and the near infrared (N) component are calculated in each pixel i by the scale search unit 411. In this case, the gradient unit 412 calculates, in each pixel i, $s_{Ri} \times \Delta R_i$, $s_{Gi} \times \Delta G_i$, $s_{Bi} \times \Delta B_i$, and $s_{Ni} \times \Delta N_i$ as the gradient scores $g_{Ri}$, $g_{Gi}$, $g_{Bi}$, and $g_{Ni}$ with regard to the red (R) component, the green (G) component, the blue (B) component, and the near infrared (N) component.

The gradient finalization unit 42 has a function of finalizing the image gradient (hereinafter, also referred to as a target gradient) for each pixel i in the combined image, when the scalar image and the near-infrared image are combined, by using the gradient score calculated by the gradient unit 412. In other words, the gradient finalization unit 42 finalizes the target gradient by using not only the information on each of the image gradients in the scalar image and the near-infrared image but also the gradient score in consideration of the scale score (the information related to the spatial frequency).

For example, the gradient finalization unit 42 selects a component (channel) with the highest score among the gradient scores $g_{Ri}$, $g_{Gi}$, $g_{Bi}$, and $g_{Ni}$ in each pixel i, and finalizes the image gradient used for calculating the gradient score of the selected component (channel) as the target gradient $\Delta J_i$. As a specific example, when the component (channel) with the largest score among the gradient scores $g_{R5}$, $g_{G5}$, $g_{B5}$, and $g_{N5}$ of an image $_5$(i=5) is red, "$\Delta R_5$" of $g_{R5}$ $s_{R5} \times \Delta R_5$ is finalized as the target gradient $\Delta J_5$.

Note that the calculation method of the target gradient $\Delta J_i$ is not limited to the above-described method. The gradient finalization unit 42 may calculate, for example, the target gradient $\Delta J_i$, based on the information on the image gradient calculated by the gradient calculation unit 40, the gradient score calculated by the gradient unit 412, and the following equation (4). In other words, the gradient finalization unit 42 may calculate the target gradient $\Delta J_i$ by weighted averaging the calculated gradient scores with the image gradients for each pixel.

$$\Delta J_i = g_{Ri} \times \Delta R_i + g_{Gi} \times \Delta G_i + g_{Bi} \times \Delta B_i + s_{Ni} \times \Delta N_i \quad \text{Equation (4):}$$

The coefficient calculation unit 43 has a function of calculating a coefficient of the base vector $\varphi_{ji}$ constituting the base vector group $\Phi_i$, when the scalar image and the near-infrared image are combined, by using the target gradient $\Delta J_i$ of each pixel i defined by the gradient finalization unit 42 in each pixel i of the combined image. For example, the coefficient calculation unit 43 calculates, when the coefficient of the base vector $\varphi_j$ of the base vector group $\Phi_i$ in the pixel i is the value of $\lambda_i$ that minimizes a square error E ($\lambda_j$) represented by the following equation (5) as a coefficient of the base vector $\varphi_i$.

$$E(\lambda_j) = |\Sigma_j ((\Delta \Phi_i) \times \lambda_j \Delta J_i)^2| \quad \text{Equation (5):}$$

Note that $\Delta \Phi_i$ in the equation (5) represents the image gradient (herein, for example, a gradient of base vector $\varphi_j$) of the base vector group $\Phi_i$ in the pixel i. $\Delta J_i$ represents the target gradient calculated by the gradient finalization unit 42.

The combination unit 44 has a function of generating a combined image by linear combination of the base vector, based on the coefficient $\lambda_{ji}$ of the base vector $\varphi_{ji}$ in each pixel i calculated by the coefficient calculation unit 43.

The processing device 4 generates a combined image of the scalar image and the near-infrared image described above. The output unit 6 is an interface device and, for example, is connected to a display device 8 and has an interface function of outputting information on the scalar image, the near-infrared image, and the combined image to the display device 8. The display device 8 has a function of displaying the scalar image, the near-infrared image, and the combined image on the display, based on the information of the image output from the output unit 6.

Figure 2:
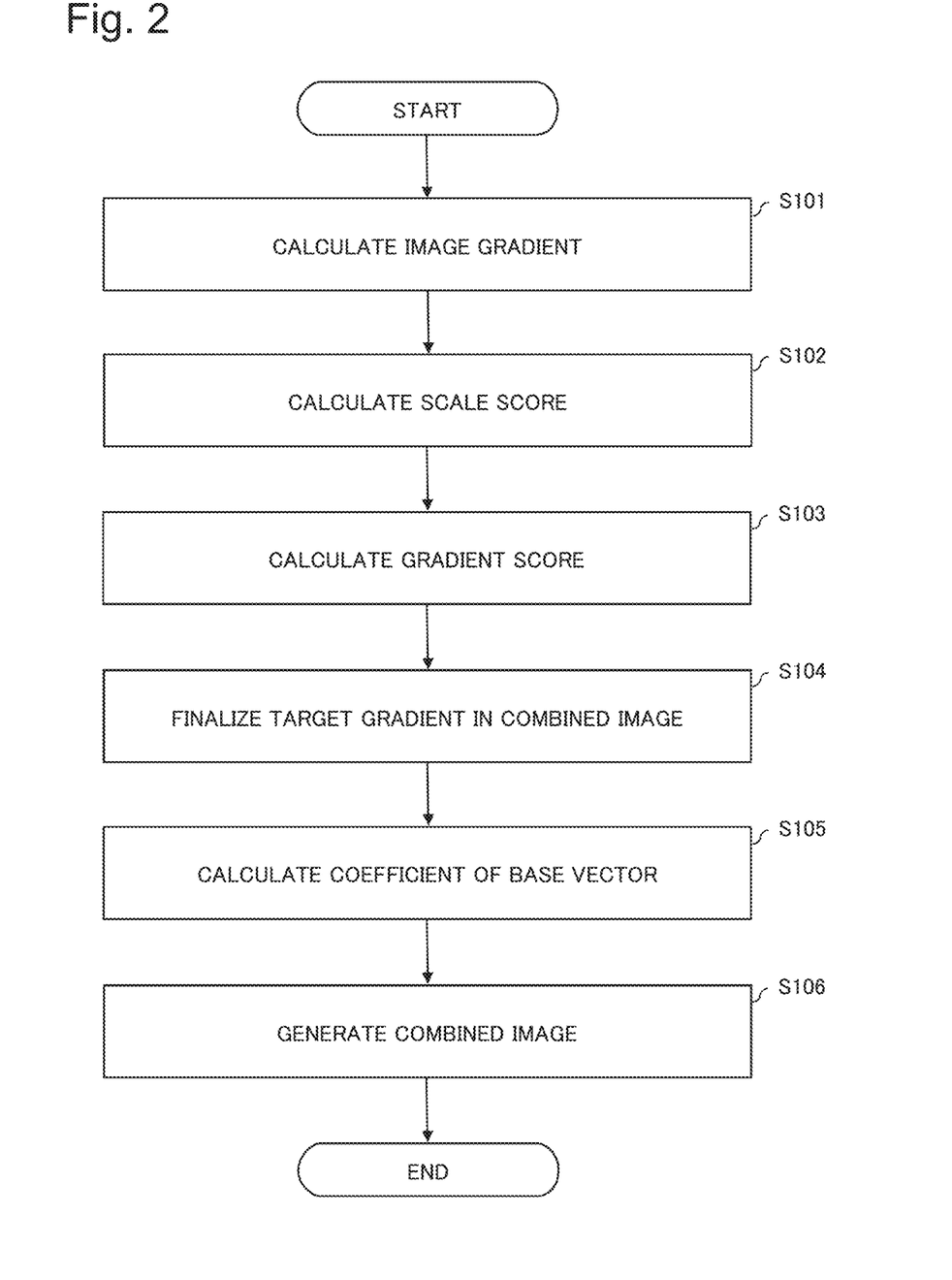
FIG. 2 is a flowchart illustrating an operation example of image combination in the image processing device according to the first example embodiment.

Next, one example of the processing operation relating to the generation of a combined image in the processing device 4 is described, based on a flowchart in FIG. 2.

For example, the gradient calculation unit 40 of the processing device 4 reads a scalar image and a near-infrared image to be combined, for example, from the storage unit 5. Then, the gradient calculation unit 40 calculates an image gradient of each pixel, in each of the read scalar image and the near-infrared image (step S101).

Further, the scale search unit 411 in the score calculation unit 41 calculates a scale score of each pixel, in each of the scalar image and the near-infrared image to be combined (step S102).

Then, the gradient unit 412 in the score calculation unit 41 calculates a gradient score depending on magnitude of the calculated image gradient and the scale score, in each pixel of each of the scalar image and the near-infrared image (step S103).

Then, the gradient finalization unit 42 finalizes a target gradient of each pixel in the combined image of the scalar image and the near-infrared image, by using the gradient score calculated by the gradient unit 412 (step S104).

Then, the coefficient calculation unit 43 calculates a coefficient of the base vector constituting the base vector group, by using the finalized target gradient (step S105). And then, the combination unit 44 generates a combined image by linear combination of the base vector, based on the coefficient of the base vector calculated by the coefficient calculation unit 43 (step S106).

By including the above-described configuration, the image processing device 1 according to the first example embodiment can produce the following advantageous effect. Specifically, the processing device 4 in the image processing device 1 calculates, when combining a plurality of images, information related to a spatial frequency in each pixel of these images as a scale score, and calculates a gradient score of each pixel in a combined image in consideration of the scale score. Then, the processing device 4 generates, by using the calculated gradient score, the combined image by calculating a coefficient of the base vector of each pixel. In other words, the processing device 4 generates a combined image in consideration of even the information on a spatial frequency in each image before combining. Therefore, the processing device 4 (the image processing device 1) is able to improve image quality of a combined image.

Figure 3:
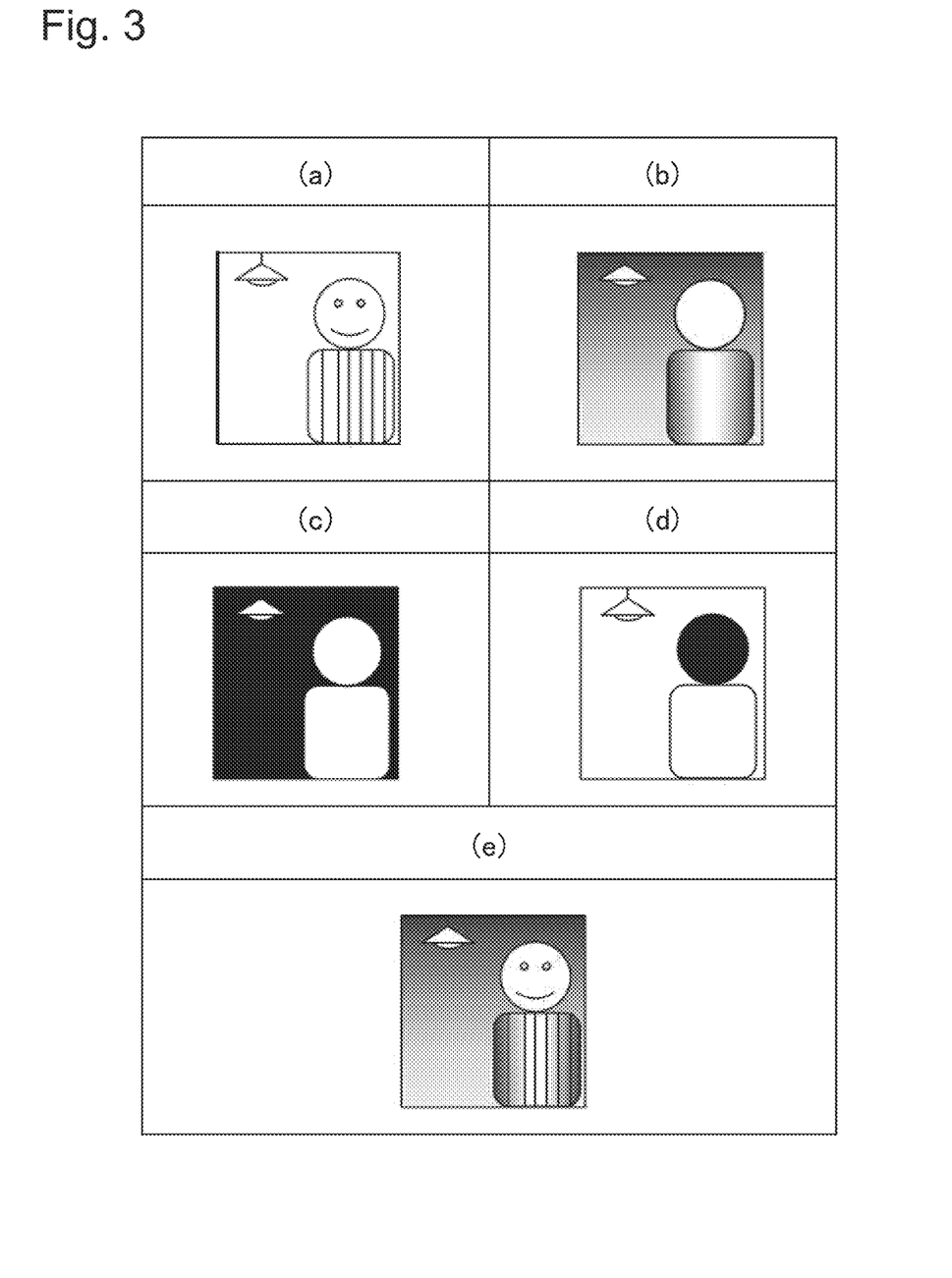
FIG. 3 is a diagram illustrating an advantageous effect produced by image combination processing in the image processing device according to the first example embodiment.

In FIG. 3, for example, it is assumed that a scalar image as illustrated in part (a) and a near-infrared image with little texture and including gradation as illustrated in part (b) are combined by using the method in NPL 1 described above. In this case, information on the gradation in the near-infrared image does not appear in the combined image. On the other hand, according to the first example embodiment, information related to a spatial frequency is calculated as a scale score and a gradient score is calculated by using the scale score. The part (c) in FIG. 3 represents one example of magnitude of the gradient score for each pixel in the scalar image of the part (a) by the degree of black and white, and the part (d) represents one example of magnitude of the gradient score for each pixel in the near-infrared image of the part (b) by the degree of black and white. In the parts (c) and (d) of FIG. 3, the gradient score is represented by the degree of black and white in such a way that the image becomes white as the gradient score becomes larger (becomes black as the gradient score becomes smaller). As illustrated in the part (d) of FIG. 3, a high gradient score is given to the part containing the gradation, and thereby generating a combined image in which the gradation information is reflected, like the combined image illustrated in the part (e) of FIG. 3.

As described above, when a plurality of images are combined, the image processing device 1 (processing device 4) according to the first example embodiment is able to acquire, by using information on an image gradient, an advantageous effect of being able to generate a combined image to be easily analyzed, for example, by an analyst that performs image analysis by using a combined image. In addition, the image processing device 1 according to the first example embodiment generates a combined image by using even information (scale) on a spatial frequency, thereby generating a combined image reflecting even information on gradation that changes globally, and therefore improvement of image quality required for a combined image can be achieved.

Other Example Embodiments

Note that this invention is not limited to the first example embodiment and various example embodiments are applicable. According to the first example embodiment, for example, a base vector constituting a base vector group in consideration of an image as a whole is set. Instead of this, for example, a base vector constituting a base vector group by focusing on some area of an image may be set. Further, after a large number of base vectors constituting a base vector group, for example as represented in the equation (1), are set, the number of the base vectors is reduced by using, for example, a main component analysis or a non-negative matrix factorization, and thus the base vector of the base vector group may be set.

Further, an image may be divided into a plurality of divided areas, the image processing as described above may be performed for each divided area, and a combined image may be generated for each divided area. In this case, for example, a base vector group may be set for each divided area of the image. Further, when the base vector group is set for each divided area in this way, the following processing may be performed for each divided area, after calculating a coefficient of a base vector constituting the base vector group, similarly to the first example embodiment. For example, the coefficient calculation unit 43 further calculates a coefficient of the base vector that minimizes the optimization function represented in the following equation (6) in consideration of the spatial smoothing between the divided areas, and finalizes the calculated coefficient as the coefficient of the base vector of each pixel in consideration of the combined image as a whole.

$$F(\lambda_{ji}) = |\lambda_{ji} - \lambda_{ji0}|^2 + |\Delta\lambda_{ji} - \Delta\Delta_{ji0}|^2 \qquad \text{Equation (6):}$$

Note that $\lambda_{ji}$ in the equation (6) represents the coefficient of the j-th base vector of the base vector group in the pixel i that the coefficient calculation unit 43 finalizes by using the equation (6). $\lambda_{ji0}$ is similar to the coefficient $\lambda_{ji}$ being calculated by the coefficient calculation unit 43 as described according to the first example embodiment, and herein, is represented as $\lambda_{ji0}$ for convenience. $\Delta\lambda_{ji}$ represents a gradient of the coefficient $\lambda_{ji}$ and $\Delta\lambda_{ji0}$ represents a gradient of $\lambda_{ji0}$.

Note that, instead of the equation (6), the following equation (7) may be employed to finalize the coefficient of the base vector of each pixel in the divided area.

$$F(\lambda_{ji}) = |\lambda_{ji} - \lambda_{ji0}|^2 + |\Delta\lambda_{ji}|^p \qquad \text{Equation (7):}$$

Note that p in the equation (7) represents a constant being an integer greater than or equal to 0. This p is set appropriately.

Further, the first example embodiment is described by the example of combining a scalar image (a visible light image) and a near-infrared image, however like combining a scalar image and a far-infrared image, in the image processing device 1 according to the first example embodiment, the combination of a plurality of images to be combined is not limited to the combination described according to the first example embodiment. Further, the processing of combining image to be performed by the image processing device 1 is not limited to combining two images, and the processing is also applied to combining three or more images.

Figure 4:
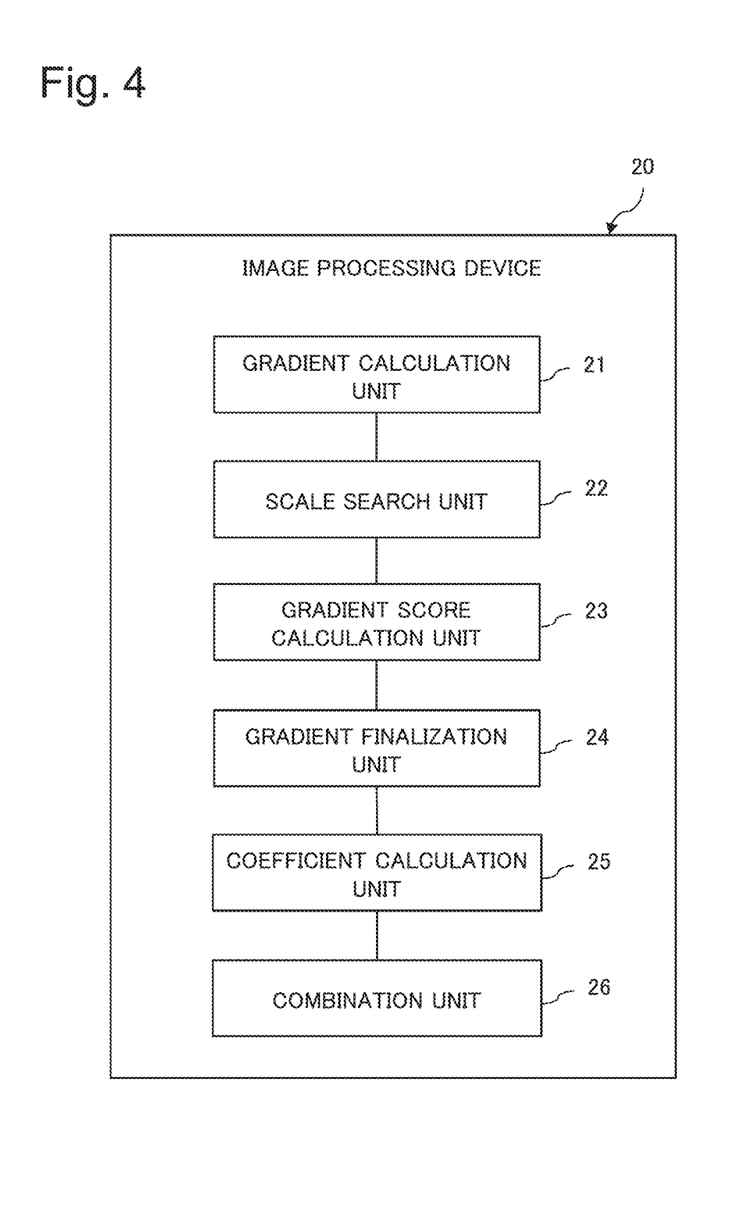
FIG. 4 is a diagram illustrating another example embodiment according to the present invention.

Further, the image processing device according to the present invention is not limited to the configuration of the first example embodiment, but may have a configuration as illustrated in a block diagram of FIG. 4. Specifically, the image processing device 20 illustrated in FIG. 4 includes a gradient calculation unit 21, a scale search unit 22, a gradient score calculation unit 23, a gradient finalization unit 24, a coefficient calculation unit 25, and a combination unit 26.

The gradient calculation unit 21 has a function of calculating an image gradient for each pixel in each of a plurality of images to be combined. The scale search unit 22 has a function of calculating a scale score, based on an inclusion degree of a spatial frequency component for each pixel in each image to be combined. The gradient score calculation unit 23 has a function of calculating, for each pixel, a gradient score depending on magnitude of the calculated image gradient and the scale score.

The gradient finalization unit 24 compares the gradient scores of associated pixels in the plurality of images to be combined, and has a function of calculating an image gradient depending on the gradient score of an image having a larger gradient score than other images among the plurality of images to be combined as a target gradient for each pixel in the combined image after combining the plurality of images to be combined.

The coefficient calculation unit 25 has a function of calculating, for each pixel of the combined image, a coefficient of a base vector constituting a base vector group predetermined in a combined image, based on the target gradient. The combination unit 26 has a function of generating the combined image by linear combination of the base vector, based on the calculated coefficient.

Also in the image processing device 20, a combined image is generated in consideration of the spatial frequency component similarly to the first example embodiment, and therefore similar advantageous effect to the first example embodiment can be acquired.

In the foregoing, the present invention is described by the above-described example embodiments as exemplary examples. The present invention, however, is not limited to the above-described example embodiments. Specifically, the present invention is applicable to various aspects comprehensible to a person skilled in the art within the scope of the present invention.

REFERENCE SIGNS LIST

1, 20 Image processing device
21, 40 Gradient calculation unit
22, 411 Scale search unit
23 Gradient score calculation unit
24, 42 Gradient finalization unit
25, 43 Coefficient calculation unit
26, 44 Combination unit
412 Gradient unit

What is claimed is:
1. An image processing device comprising:
at least one processor configured to:
calculate an image gradient for each pixel in each of a plurality of images to be combined;
calculate a scale score based on an inclusion degree of a spatial frequency component for the each pixel in the each of the plurality of images to be combined;
calculate, for the each pixel, a gradient score depending on the calculated image gradient and the calculated scale score;
compare the gradient scores of associated pixels in the plurality of images to be combined, and calculate a target gradient for each pixel in a combined image after combining the plurality of images to be combined, the target gradient being the image gradient depending on the gradient score of the image having the larger gradient score than other images among the plurality of images to be combined;
calculate, for the each pixel of the combined image, a coefficient of a base vector constituting a base vector group predetermined in the combined image based on the target gradient; and
generate the combined image by linear combination of the base vector based on the calculated coefficient.

2. The image processing device according to claim 1, wherein the at least one processor calculates the coefficient of the base vector for each pixel in each divided area of a plurality of areas into which the combined image is divided, and performs processing in consideration of spatial smoothing between the divided areas to the calculated coefficient, and finalizes the coefficient of the base vector in consideration of the combined image as a whole.

3. The image processing device according to claim 1, wherein the at least one processor compares gradient scores calculated in the plurality of images to be combined, and finalizes the image gradient of the image having a largest gradient score, as the target gradient.

4. The image processing device according to claim 1, wherein the at least one processor calculates the target gradient by weighting and averaging the calculated gradient scores with the image gradients for the each pixel.

5. The image processing device according to claim 1, wherein the at least one processor calculates, when calculating the coefficient of the base vector in the combined image, a coefficient that minimizes a square error related to the image gradient, as the coefficient of the base vector.

6. An image processing method, comprising:
by at least one processor,
calculating an image gradient for each pixel in each of a plurality of images to be combined;
calculating a scale score based on an inclusion degree of a spatial frequency component for the each pixel in the each of the images to be combined;
calculating, for the each pixel, a gradient score depending on the calculated image gradient and the calculated scale score;
comparing the gradient scores of associated pixels in the plurality of images to be combined, and calculating a target gradient for each pixel in a combined image after combining the plurality of images to be combined, the target gradient being the image gradient depending on the gradient score of the image having the larger gradient score than other images among the plurality of images to be combined;
calculating, for the each pixel of the combined image, a coefficient of a base vector constituting a base vector group predetermined in the combined image based on the target gradient; and
generating the combined image by linear combination of the base vector based on the calculated coefficient.

7. A non-transitory program storage medium storing a computer program that causes a computer to execute:
calculating an image gradient for each pixel in each of a plurality of images to be combined;
calculating a scale score based on an inclusion degree of a spatial frequency component for the each pixel in the each of the images to be combined;
calculating, for the each pixel, a gradient score depending on the calculated image gradient and the calculated scale score;
comparing the gradient scores of associated pixels in the plurality of images to be combined, and calculating a target gradient for each pixel in a combined image after combining the plurality of images to be combined, the target gradient being the image gradient depending on the gradient score of the image having the larger gradient score than other images among the plurality of images to be combined;
calculating, for the each pixel of the combined image, a coefficient of a base vector constituting a base vector group predetermined in the combined image based on the target gradient; and
generating the combined image by linear combination of the base vector based on the calculated coefficient.

* * * * *